United States Patent
Tanaka et al.

(10) Patent No.: US 9,550,073 B2
(45) Date of Patent: Jan. 24, 2017

(54) THERAPEUTIC AGENT FOR ALLERGIC RHINITIS

(75) Inventors: Tohru Tanaka, Tokyo (JP); Katsushi Inoue, Tokyo (JP); Kiwamu Takahashi, Tokyo (JP); Takuya Ishii, Tokyo (JP); Tsutomu Numata, Chiba (JP); Mariko Shibuya, Chiba (JP); Takeshi Suzuki, Chiba (JP)

(73) Assignees: SBI Pharmaceuticals Co., Ltd., Tokyo (JP); National Hospital Organization, Tokyo (JP)

( * ) Notice: Subject to any disclaimer, the term of this patent is extended or adjusted under 35 U.S.C. 154(b) by 119 days.

(21) Appl. No.: 14/125,744

(22) PCT Filed: Jun. 15, 2012

(86) PCT No.: PCT/JP2012/003945
§ 371 (c)(1),
(2), (4) Date: Mar. 13, 2014

(87) PCT Pub. No.: WO2012/172821
PCT Pub. Date: Dec. 20, 2012

(65) Prior Publication Data
US 2014/0188034 A1 Jul. 3, 2014

(30) Foreign Application Priority Data

Jun. 16, 2011 (JP) .................................. 2011-134489

(51) Int. Cl.
*A61N 5/06* (2006.01)
*A61K 9/06* (2006.01)
*A61K 41/00* (2006.01)
*A61K 9/00* (2006.01)

(52) U.S. Cl.
CPC ............. *A61N 5/062* (2013.01); *A61K 9/0043* (2013.01); *A61K 9/06* (2013.01); *A61K 41/0061* (2013.01); *F04C 2270/0421* (2013.01)

(58) Field of Classification Search
None
See application file for complete search history.

(56) References Cited

U.S. PATENT DOCUMENTS

| | | | | |
|---|---|---|---|---|
| 6,520,384 B2* | 2/2003 | Mehta | ............................ | 222/211 |
| 8,173,839 B2* | 5/2012 | Tachiya | ................. | A01N 37/44 |
| | | | | 562/567 |
| 8,471,061 B2* | 6/2013 | Tachiya | ................. | A01N 37/44 |
| | | | | 562/567 |
| 8,790,712 B2* | 7/2014 | Kondo | ................. | A23K 1/1634 |
| | | | | 424/630 |
| 8,927,532 B2* | 1/2015 | Kuroiwa | ............. | A61K 31/197 |
| | | | | 514/184 |
| 8,999,296 B2* | 4/2015 | Inoue | ................. | A61K 41/0061 |
| | | | | 424/463 |
| 9,012,502 B2* | 4/2015 | Chibazakura | ........ | A61K 31/197 |
| | | | | 514/551 |
| 9,089,530 B2* | 7/2015 | Tanaka | ................. | A61K 31/197 |
| 9,095,165 B2* | 8/2015 | Tanaka | | |

FOREIGN PATENT DOCUMENTS

| | | |
|---|---|---|
| CA | 2461070 C | 10/1993 |
| JP | 2731032 B2 | 12/1997 |
| JP | 2005-501050 A | 1/2005 |
| JP | 2006-124372 A | 5/2006 |
| WO | WO 91/01727 A2 | 2/1991 |
| WO | WO 93/20810 A2 * | 10/1993 |
| WO | WO 03/011265 A2 | 2/2003 |

OTHER PUBLICATIONS

Merriam-Webster Dictionary [Online]. "Transdermal". [Retrieved Jul. 23, 2015]. Retrieved from the Internet: <URL: http://www.merriam-webster.com/dictionary/transdermal>.*

Tokuoka et al. "EST Spectroscopy of Singlet Oxygen Generated by Protoporphyrin IX in Aqueous Surfactant Solutions". J. Oleo Sci. 2003; 52(3);135-140.*

Csoma et al., "PUVA Treatment of the Nasal Cavity Improves the Clinical Symptoms of Allergic Rhinitis and Inhibits the Immediate-type Hypersensitivity Reaction in the Skin," Journal of Photochemistry and Photobiology B: Biology, 2006, 83:21-26.

(Continued)

*Primary Examiner* — Leslie A. Royds Draper
(74) *Attorney, Agent, or Firm* — Foley & Lardner LLP

(57) ABSTRACT

Provided is a therapeutic agent capable of treating allergic rhinitis in a safe, simple, and noninvasive manner substantially without side effects and physical distress to patients. Provided is a therapeutic agent for allergic rhinitis for 5-aminolevulinic acid-based photodynamic therapy (ALA-PDT) comprising 5-aminolevulinic acid (ALA) or a derivative thereof, or a salt of the 5-aminolevulinic acid or the derivative as an active ingredient, and used in ALA-PDT in which light having a wavelength of 400 nm to 700 nm is irradiated; and particularly provided is a therapeutic agent for allergic rhinitis in a locally applied solution form, a water-soluble ointment-dissolved form, a jelly-dissolved form, or the like. The therapeutic agent does not require the conduct of 5-aminolevulinic acid-based photodynamic diagnosis (ALA-PDD) for detecting a site of protoporphyrin IX (PpIX) accumulation radiating light having a wavelength of 610 nm to 650 nm under irradiation of excitation light having a wavelength of 380 nm to 420 nm before ALA-PDT.

8 Claims, 2 Drawing Sheets

(56) References Cited

OTHER PUBLICATIONS

Kennedy et al., "Photodynamic Therapy with Endogenous Protoporphyrin, IX: Basic Principles and Present Clinical Experience," Journal of Photochemistry and Photobiology B: Biology, 1990, 6:143-148.

Bexfield et al., "Photodynamic Therapy to Superficial Nasal Planum Squamous Cell Carcinomas in Cats: 55 Cases," Journal of Veterinary Internal Medicine, Nov. 1, 2008, 22(6):1385-1389.

\* cited by examiner

THERAPEUTIC AGENT FOR ALLERGIC RHINITIS

CROSS-REFERENCE TO RELATED APPLICATIONS

This application is a National Stage application of PCT/JP2012/003945, filed Jun. 15, 2012, which claims priority from Japanese application JP 2011-134489, filed Jun. 16, 2011.

TECHNICAL FIELD

The present invention relates to a therapeutic agent for allergic rhinitis, comprising 5-aminolevulinic acid (hereinafter also referred to as "ALA or δ-aminolevulinic acid") or a derivative thereof, or a salt of the 5 aminolevulinic acid or the derivative (hereinafter which are also collectively referred to as "ALAS") as an active ingredient and used in 5-aminolevulinic acid-based photodynamic therapy (hereinafter also referred to as "ALA-PDT") in which light having a wavelength of 400 nm to 700 nm, preferably 625 nm to 640 nm, is irradiated.

BACKGROUND ART

Allergic rhinitis is caused by the response of the autoimmune system in the body to a causative agent in the external environment, and dust, mold, pollen, or the like is known as the causative agent.

A drug therapy, a desensitization therapy, an operative therapy by inferior concha cauterization using a laser, or the like is known as a therapeutic method for allergic rhinitis represented by pollinosis. For the drug therapy, a steroidal anti-inflammatory drug, an immunosuppressive drug, an antihistamine drug, or the like is used; however, this therapy is known to have problems in terms of side effects and efficacy. For example, it is considered problematic in that the steroidal anti-inflammatory drug has side effects such as adrenal atrophy and dysfunction and gastric ulcer (see, for example, Non-patent Document 1), that the immunosuppressive drug has side effects such as infection (see, for example, Non-patent Document 2), and that the antihistamine drug has side effects such as malaise, drowsiness, and dizziness. The antihistamine drug is also known to be unsatisfactory in terms of efficacy compared to the steroidal anti-inflammatory drug and the immunosuppressive drug.

The desensitization therapy is known as a method for suppressing only a concerned antigen-specific immune response by specifying an antigen responsible for allergy and intradermally administering the antigen to induce desensitization; however, it is considered to take several months to several years to exert a sufficient effect. In addition, this therapy is known to have a risk of inducing anaphylactic shock or the like due to the direct systemic administration of an antigen causing allergy, making it necessary to gradually increase its dose from a low dose. In other words, the desensitization therapy is considered problematic in that it not only requires a long-term treatment but also is accompanied by a patient's distress due to injection.

The operative therapy by inferior concha cauterization using a laser is considered problematic in that it not only inflicts a physical distress on patients with allergic rhinitis but also is not a method for radically treating allergic rhinitis.

On the other hand, recently, PDT has been developed that is a method involving administering a compound responsive to light and treating a target area by light irradiation. PDT is simple in treatment, exhibits low invasiveness into a living body, and enables the conservation of an organ, for example; thus, it has recently been a focus of attention as a new method for treating cancer in which consideration is given to quality of life (QOL).

ALA as one of the drugs used for PDT is known as an intermediate in a pathway of pigment biosynthesis broadly present in animals, plants, and fungi, and is typically biosynthesized from succinyl-CoA and glycine by 5-aminolevulinic acid synthetase. Although ALA has no photosensitivity per se, it is known that ALA is metabolically activated to protoporphyrin IX (hereinafter also referred to as "PpIX") by a series of enzymes of the heme biosynthetic pathway in cells and then specifically directly accumulates in tumor tissue and neovascular vessels, and that, when laser light is irradiated on the site in which PpIX accumulates, cancer cells are degenerate/necrotize by reactive oxygen species generated by the excitation of light, which are represented by singlet oxygen, hydroxyl radical, superoxide, and the like.

Since Professor Kennedy of Queen's University, Canada, reported in 1986 that skin cancer can be treated by applying ALA and irradiating light (see, for example, Non-patent Document 3), methods have been reported for diagnosing and treating lesioned parts of various sites using ALA. For example, tumor diagnosing agents are proposed which have been developed based on the finding that, when ALAs is administered into the body, PpIX derived from the ALAs accumulates in cancer and emits fluorescence by light irradiation (see, for example, Patent Documents 1 and 2).

Because PpIX emits red fluorescence having a peak at a wavelength of 636 nm when receiving excitation light having a wavelength around 410 nm, ALAs are used for the diagnosis of tumor by 5-aminolevulinic acid-based photodynamic diagnosis (ALA-PDD), and is also expected to be used in applications such as the diagnosis of brain tumor or bladder cancer and the prevention of anemia.

PRIOR ART DOCUMENTS

Patent Documents

Patent Document 1: Japanese Patent No. 2731032
Patent Document 2: Japanese unexamined Patent Application Publication No. 2006-124372

Non-Patent Documents

Non-patent Document 1: Zenro Ikezawa, Arerugi Shikkan (Allergic Disease), Japanese Journal of Pediatrics, 1998, Nihon Shoni Iji Shuppan Co., Ltd.
Non-patent Document 2: Hidenori Fukunaka et al., Kou Arerugi Yaku (Anti-allergic Drug), Clinic All-Round, 1997, Nagai Shoten Co., Ltd.
Non-patent Document 3: J. C Kennedy, R. H Pottier and D C Pross, Photodynamic therapy with endogeneous protoprophyrin IX: basic principles and present clinical experience, J. Photochem., Photobiol. B: Biol., 6 (1990) 143-148

SUMMARY OF THE INVENTION

Object to be Solved by the Invention

An object of the present invention is to provide a therapeutic agent capable of treating allergic rhinitis in a safe, simple, and noninvasive manner substantially without side effects and physical distress to patients.

Means to Solve the Object

Cancer treatment using ALA-PDT has been widely studied, and the present inventors also have proceeded with intensive research thereon for many years. The cancer treatment using ALA-PDT is known as a therapy based on the fact that more PpIX is produced/accumulates in cancer cells than in normal cells; however, a detailed mechanism by which more PpIX is produced/accumulates in cancer cells has not ever been elucidated. Little has also been known about whether ALA accumulates outside cancer cells and cancer tissue. The present inventors have exhaustively studied the possibility of using ALA-PDT for the treatment of all diseases, during which allergic rhinitis also happened to be studied. When ALA was orally administered to patients with allergic rhinitis due to pollinosis on trial, PpIX was found to accumulate in an inflamed site of the nasal mucosa. Accordingly, when PDT was applied to the site of PpIX accumulation, it was confirmed to have therapeutic effect against allergic rhinitis. In addition, the therapeutic effect against allergic rhinitis was observed even when it was transdermally administered, i.e. applied in a solution form, rather than being orally administered. The present invention has been accomplished based on these findings.

Specifically, the present invention relates to: (1) a therapeutic agent for allergic rhinitis, comprising 5-aminolevulinic acid (ALA) or a derivative thereof, or a salt of the 5-aminolevulinic acid or the derivative as an active ingredient, for use in 5-aminolevulinic acid-based photodynamic therapy (ALA-PDT) in which light having a wavelength of 400 nm to 700 nm is irradiated; (2) the therapeutic agent for allergic rhinitis according to (1) above, wherein light having a wavelength of 625 nm to 640 nm is irradiated; (3) the therapeutic agent for allergic rhinitis according to (1) or (2) above, wherein the therapeutic agent is orally administered; (4) the therapeutic agent for allergic rhinitis according to (1) or (2) above, wherein the therapeutic agent is transdermally administered into a nasal cavity; and (5) the therapeutic agent for allergic rhinitis according to (4) above, wherein the therapeutic agent is transdermally administered in an applied solution form, a water-soluble ointment-dissolved form, or a jelly-dissolved form.

The embodiments of the present invention include: [1] a method for treating allergic rhinitis by ALA-PDT involving administering ALAs and irradiating light having a wavelength of 400 nm to 700 nm into the nasal cavity; [2] the method for treating allergic rhinitis according to [1] above, wherein light having a wavelength of 625 nm to 640 nm is irradiated; [3] a method for using ALAs for treating allergic rhinitis by ALA-PDT involving irradiating light having a wavelength of 400 nm to 700 nm into the nasal cavity; [4] the method for using ALAs for treating allergic rhinitis according to [3] above, wherein light having a wavelength of 625 nm to 640 nm is irradiated; [5] use of ALAs for preparing a drug for treating allergic rhinitis by ALA-PDT involving irradiating light having a wavelength of 400 nm to 700 nm into the nasal cavity; [6] the use of ALAs for preparing a drug for treating allergic rhinitis according to [5] above, wherein light having a wavelength of 625 nm to 640 nm is irradiated; [7] a therapeutic system for allergic rhinitis, comprising an ALA-PDD device and an ALA-PDT device or comprising an ALA-PDT device, used for the treatment of allergic rhinitis successively comprising (a) an ALA administration step of administering ALAS; (b) an ALA-PDD step of determining a site of PpIX accumulation by irradiating excitation light having a wavelength of 380 nm to 420 nm and detecting red fluorescence; and (c) an ALA-PDT step of irradiating light having a wavelength of 400 nm to 700 nm on the site of PpIX accumulation; and [8] the therapeutic system for allergic rhinitis according to [7] above, wherein the ALA-PDT step involves irradiating light having a wavelength of 625 nm to 640 nm.

Effect of the Invention

The use of the therapeutic agent for allergic rhinitis of the present invention can treat allergic rhinitis in a safe, simple, and noninvasive manner substantially without side effects and physical distress to patients. The burden on patients is also reduced because its therapeutic effect against allergic rhinitis can be maintained for at least 1 year.

MODE OF CARRYING OUT THE INVENTION

Figure 1:
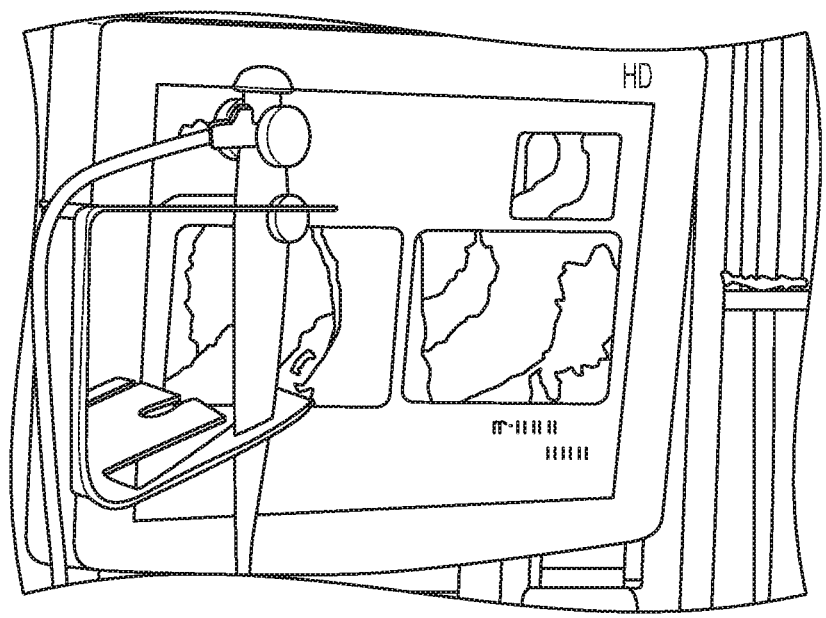
FIG. 1 shows the results of confirming PpIX accumulation in an inflamed site of the nasal mucosa by ALA-PDD using a bronchoscope (Pentax SAFE-3000). The left side shows an image under normal illumination, and the right side shows a PpIX fluorescence image under the illumination of violet light having a wavelength of 408 nm.

The therapeutic agent for allergic rhinitis according to the present invention is not particularly limited provided that it comprises ALAs, which is ALA or a derivative thereof, or a salt of the ALA or the derivative, as an active ingredient and is a therapeutic agent for ALA-PDT used in ALA-PDT in which light having a wavelength of 400 nm to 700 nm, preferably 625 nm to 640 nm, is irradiated, and may be a therapeutic agent with which ALA-PDD is performed involving detecting a site of PpIX accumulation radiating light having a wavelength of 610 nm to 750 nm by irradiating excitation light having a wavelength of 380 nm to 420 nm, before ALA-PDT in which light having a wavelength of 400 nm to 700 nm, preferably 625 nm to 640 nm, is irradiated; however, a therapeutic agent not requiring the conduct of such a preceding ALA-PDD can be particularly preferably exemplified. The therapeutic system using the therapeutic agent for allergic rhinitis according to the present invention is not particularly limited provided that it is a system comprising an ALA-PDT device, and may be one comprising an administration device for ALAs and ALA-PDD.

ALA and a derivative thereof are represented by formula (I) below (wherein $R^1$ represents a hydrogen atom or an acyl group, and $R^2$ represents a hydrogen atom, a straight-chain or branched alkyl group, a cycloalkyl group, an aryl group, or an aralkyl group).

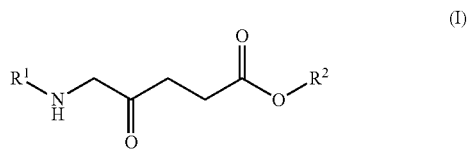

Among ALAs, ALA in which $R^1$ and $R^2$ in the formula (I) each represent a hydrogen atom, or a salt thereof can be preferably exemplified. ALA is one amino acid also called δ-aminolevulinic acid. Examples of the ALA derivative include compounds other than 5-ALA, in each of which $R^1$ in the formula (I) represents a hydrogen atom or an acyl group and $R^2$ in the formula (I) represents a hydrogen atom, a straight-chain or branched alkyl group, a cycloalkyl group, an aryl group, or an aralkyl group.

Examples of the acyl group in the formula (I) include straight-chain or branched alkanoyl groups each having 1 to 8 carbon atoms, such as formyl group, acetyl group, propionyl group, butyryl group, isobutyryl group, valeryl group, isovaleryl group, pivaloyl group, hexanoyl group, octanoyl group, and benzylcarbonyl group, and aroyl groups each having 7 to 14 carbon atoms, such as benzoyl group, 1-naphthoyl group, and 2-naphthoyl group.

Examples of the alkyl group in the formula (I) include straight-chain or branched alkyl groups each having 1 to 8 carbon atoms, such as methyl group, ethyl group, propyl group, isopropyl group, butyl group, isobutyl group, sec-butyl group, tert-butyl group, pentyl group, isopentyl group, neopentyl group, hexyl group, heptyl group, and octyl group.

Examples of the cycloalkyl group in the formula (I) include cycloalkyl groups each having 3 to 8 carbon atoms, which are saturated or may optionally contain an unsaturated bond(s) in part, such as cyclopropyl group, cyclobutyl group, cyclopentyl group, cyclohexyl group, cycloheptyl group, cyclooctyl group, cyclododecyl group, and 1-cyclohexenyl group.

Examples of the aryl group in the formula (I) include aryl groups each having 6 to 14 carbon atoms, such as phenyl group, naphthyl group, anthryl group, and phenanthryl group.

The aralkyl group in the formula (I) has an aryl moiety to which the same exemplification as that of the above-described aryl group can be applied and an alkyl moiety to which the same exemplification as that of the above-described alkyl group can be applied; specific examples thereof include aralkyl groups each having 7 to 15 carbon atoms, such as benzyl group, phenethyl group, phenylpropyl group, phenylbutyl group, benzhydryl group, trityl group, naphthylmethyl group, and naphthylethyl group.

The above ALA derivative is preferably a compound in which $R^1$ represents formyl group, acetyl group, propionyl group, butyryl group, or the like, or a compound in which $R^2$ represents methyl group, ethyl group, propyl group, butyl group, pentyl group, or the like; preferred examples of the combination of $R^1$ and $R^2$ include combinations of: formyl group and methyl group; acetyl group and methyl group; propionyl group and methyl group; butyryl group and methyl group; formyl group and ethyl group; acetyl group and ethyl group; propionyl group and ethyl group; and butyryl group and ethyl group.

ALAs each need only to act in a living body as an active ingredient in the form of ALA or a derivative thereof of the formula (I), and may be administered as any of various salts or esters for the enhancement of solubility or a prodrug (precursor) capable of being decomposed by an enzyme in a living body, depending on the dosage form. Examples of the salt of ALA and a derivative thereof include pharmacologically acceptable acid addition salts, metal salts, ammonium salts, and organic amine addition salts. Examples of the acid addition salt include inorganic salts such as hydrochlorides, hydrobromates, hydroiodides, phosphates, nitrates, and sulfates, and organic acid addition salts such as formates, acetates, propionates, toluenesulfonates, succinates, oxalates, lactates, tartrates, glycolates, methanesulfonates, butyrates, valerates, citrates, fumarates, maleates, and malates. Examples of the metal salt include alkali metal salts such as lithium salts, sodium salts, and potassium salts; alkaline earth metal salts such as magnesium salts and calcium salts; and metal salts such as aluminum salts and zinc salts. Examples of the ammonium salt include alkylammonium salts such as ammonium salts and tetramethylammonium salts. Examples of the organic amine salt include salts such as triethylamine salts, piperidine salts, morpholine salts, and toluidine salts. These salts can also be used as solutions thereof at the time of use.

Among the above ALAs, preferred are ALA, various esters such as ALA methylester, ALA ethylester, ALA propylester, ALA butylester, and ALA pentylester, and hydrochlorides, phosphates and sulfates thereof; and ALA hydrochlorides and ALA phosphates can be particularly preferably exemplified.

The above ALAs can be produced by any of known methods of chemical synthesis, microbe-based production, and enzyme-based production. The ALAs may also form hydrates or solvates, and may be used singly or in a combination of two or more thereof.

When the above ALAs are each prepared as an aqueous solution, to prevent the decomposition of the ALAs, care should be exercised so that the aqueous solution does not become alkaline. When it becomes alkaline, the decomposition can be prevented by removing oxygen.

The above ALA-PDT is a method used for a therapeutic agent for allergic rhinitis, which involves, in performing PDT for treating a target area by administering a light-responsive compound and irradiating light, administering ALAs having no photosensitizative action per se, thereby causing PpIX induced via the pigment biosynthesis pathway to specifically accumulate in cells in an inflamed site of the nasal mucosa, exciting the PpIX accumulating in inflamed cells of the nasal mucosa to optically excite oxygen molecules in the surroundings, and utilizing the fact that the ensuing singlet oxygen has a cell-killing effect due to its strong oxidation power. The wavelength of light exciting the PpIX needs only to be a wavelength of red light; specific examples thereof include 400 nm to 700 nm, preferably 625 nm to 640 nm, and among them, 635 nm is preferable.

The above-described ALA-PDD which does not necessarily need to be performed but may be optionally performed is a determination method which involves, before the ALA-PDT of the present invention, specifying an inflamed site of the nasal mucosa by utilizing the fact that the irradiation of violet light on PpIX accumulating in inflamed cells of the nasal mucosa causes the emission of red fluorescence. The wavelength of the violet light may be in the range of at least 380 nm to 420 nm; examples thereof include 400 to 420 nm and 403 to 410 nm, and among them, 408 nm is preferable.

Methods for administering ALAs in the therapeutic agent of the present invention include oral administration including sublingual administration, intravenous injection including drip infusion, and transdermal administration in the form of a poultice, a suppository, an applied solution, or the like; among them, oral administration and transdermal administration into the nasal cavity are preferable; and in view of efficiency and simpleness, transdermal administration by application to an inflamed site of the nasal mucosa can be preferably exemplified. For oral administration, because PpIX abundantly accumulates in the inflamed site but is also taken up by the normal mucosa, for example, olfactory cells, sensing aroma, can be damaged by light irradiation; however, for local administration with a solution or the like, because it can be ensured that PpIX is not taken up by olfactory cells lying in the deep upper portion of the nasal cavity, side effects such as olfactory disturbance can be avoided. Formulations of the oral administration-type therapeutic agent include powders, granules, tablets, capsules, syrups, and suspensions, and those of the intravenous injection-type therapeutic agent include injections and drops. Formulations of the therapeutic agent of a type of transdermal administration into the nasal cavity include a solution form, a water-soluble ointment-dissolved form, a jelly-dissolved form, and a spray form. Specific examples of the method of transdermal administration with an applied solution form include a method which involves causing a liquid-holding material such as gauze or absorbent cotton which sufficiently contains a solution of ALAs to contact with an inflamed site of the nasal mucosa in the nasal cavity. The dose of ALAs may be such a dose that the amount of PpIX accumulated in the inflamed site of the nasal mucosa becomes an effective amount in ALA-PDT. The specific dose of ALAs is, for example, 1 mg to 1,000 mg per kg body weight, preferably 5 mg to 100 mg per kg body weight, more preferably 10 mg to 30 mg per kg body weight, still more preferably 15 mg to 25 mg per kg body weight in terms of ALA for oral administration, and the concentration of a solution of ALAs is, for example, 1% by weight to 90% by weight, preferably 2% by weight to 40% by weight, more preferably 3% by weight to 10% by weight, still more preferably 4% by weight to 6% by weight in terms of ALA for the transdermal administration with an applied solution form. When ALAs is used in the form of a solution, to prevent the decomposition of ALAs, care is preferably exercised so that the aqueous solution does not become alkaline. When it becomes alkaline, the decomposition of the active ingredient can be prevented by removing oxygen.

The therapeutic agent of the present invention may contain other optional ingredients such as other medicinal ingredients, nutrients, and carriers as required. As optional ingredients may be added, for example, pharmaceutically acceptable ordinary carriers such as crystalline cellulose, gelatin, lactose, starch, magnesium stearate, talc, vegetable and animal fat, fat and oil, gum, and polyalkylene glycol, and various compounding ingredients for preparation such as a binder, a stabilizer, a solvent, a dispersion medium, an extender, an excipient, a diluent, a pH buffering agent, a disintegrating agent, a solubilizer, a solubilizing agent, and an isotonic agent.

In the above ALA-PDT step, an ALA-PDT device is used which is capable of irradiating red light, specifically light having a wavelength of 400 nm to 700 nm, preferably a wavelength of 625 nm to 640 nm, more preferably a wavelength of 635 nm on the region of an inflamed site of the nasal mucosa to be irradiated. The light source for irradiating the above light used may be a well-known one; examples thereof include red LED (light-emitting diode), a red semiconductor laser, and a discharge lamp having a strong red emission spectrum; however, red LED can be preferably exemplified because a device therefor is compact and is advantageous in terms of cost and portability. When the red semiconductor laser is used as a light source, the power density of the laser is preferably 20 mW/cm$^2$ to 400 mW/cm$^2$, and the energy density is preferably 25 J/cm$^2$ to 100 J/cm$^2$. The laser light may be continuous light or pulsed light; however, pulsed light is more preferable in that the use of the pulsed light can decrease damage on the normal skin surface. Specific irradiation methods includes a method which involves irradiating an inflamed site of the nasal mucosa at an energy density of, for example, 100 J/cm$^2$ while observing the site using a bronchoscope capable of fluorescent observation. The irradiation diameter when the inflamed site of the nasal mucosa is irradiated is preferably 10 mm or more; and 15 mm or more is preferable because the time of irradiation on the affected area is shortened.

As described above, the therapeutic method using the therapeutic agent of the present invention is characterized by simplicity, i.e., characterized in that ALA-PDD is not required before ALA-PDT; however, ALA-PDD may also be performed. Examples of the ALA-PDD device used in the ALA-PDD step include an excitation light irradiation device for PpIX and a device for detecting red fluorescence typical of PpIX in an excited state, or a device in which these are integrated. The light irradiated from the excitation light irradiation device for PpIX is preferably light having a wavelength enabling the observation of red fluorescence typical of PpIX by the excitation of PpIX, and may be light having a wavelength of violet light close to ultraviolet light belonging to the absorption peak of PpIX belonging to the so-called Soret band, wherein it is light having at least a wavelength being in the range of 380 nm to 420 nm; examples thereof include 400 to 420 nm and 403 to 410 nm, and among them, 408 nm is preferable.

The light source for irradiating excitation light in the above ALA-PDD step used may be a well-known one; examples thereof include light sources such as a violet LED, preferably a flash/light-type violet LED and a semiconductor laser. However, violet LED for which a device is compact and is advantageous in terms of cost and portability, especially a flash/light-type violet LED and a violet semiconductor diode can be preferably exemplified. Examples of the red fluorescence detection device for detecting red fluorescence, specifically fluorescence having a wavelength of 610 nm to 750 nm, preferably 625 to 638 nm in order to detect the site of PpIX accumulation and determine the region of an inflamed site of the nasal mucosa to be irradiated include a device for visual detection and a CCD camera-based detection device.

Examples of the ALA-PDD device in which the excitation light irradiation device and the red fluorescence detection device are integrated include a small-diameter optical fiber for light source/measurement. The light source of the excitation light irradiated in the ALA-PDD step for exciting the accumulated PpIX is preferably a semiconductor laser source having a high irradiance to enable the detection of PpIX even in a minute inflamed site of the nasal mucosa and having a narrow irradiation area to enable accurate automatic discrimination; it preferably has an excitation light-guiding section for guiding the excitation light to launch it from one end to the outside; and specific examples of the excitation light-guiding section include a small-diameter optical fiber. The element used for a light source may be a semiconductor mixed crystal such as InGaN, which can oscillate violet light by changing the compounding ratio of InGaN. Specifically, a compact laser diode having a diameter of about 5.6 mm can be preferably exemplified. A device having a size of that of a desktop PC can be exemplified in which 4 laser output ports from a laser diode is connected to ports for spectrum measurement through a built-in high sensitivity spectroscope. In a light-receiving step of receiving fluorescence emitted by PpIX excited by the excitation light, a small-diameter optical fiber for measurement is used; the small-diameter optical fiber for measurement is integrated with the small-diameter optical fiber for a light source; and the received fluorescence is guided to a detector to determine the site of PpIX accumulation.

The present invention will be specifically described below with reference to Examples. However, these Examples are not intended to limit the technical scope of the present invention.

EXAMPLES

Example 1

[Treatment of Allergic Rhinitis by Oral Administration of ALA]

Figure 2:
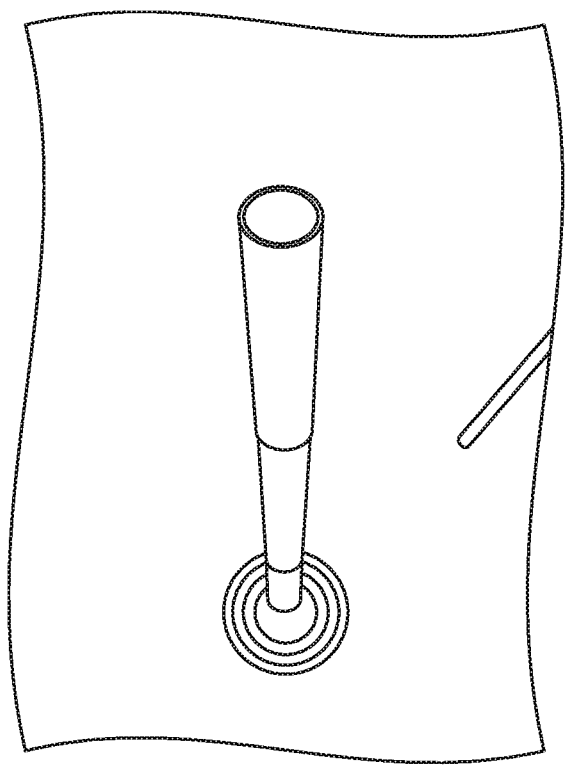
FIG. 2 shows an LED irradiation probe for PDT (φ7 mm acrylic rod light guide).
Figure 3:
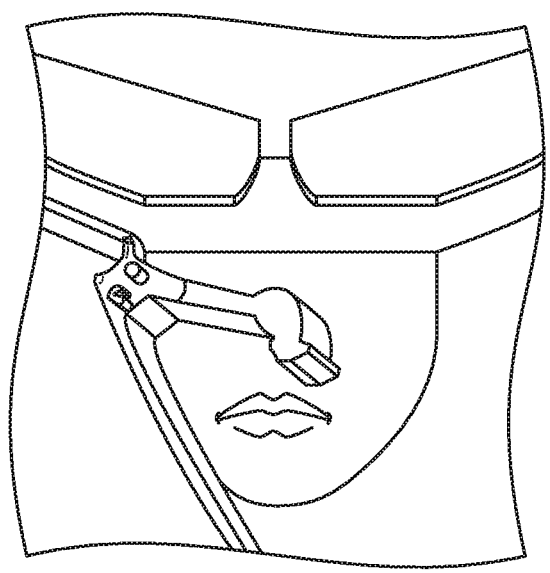
FIG. 3 shows the appearance of the procedure of PDT using an LED irradiation probe for PDT (φ7 mm acrylic rod light guide).

To 3 subject volunteers with allergic rhinitis, 20 mg/kg of ALA hydrochloride was orally administered, and violet light of 408 nm was irradiated into the nasal cavity after about 6 hours using a bronchoscope enabling fluorescence observation (SAFE-3000 from Pentax) to perform ALA-PDD. As a result, an inflamed site of the nasal mucosa by which PpIX was taken up was detected as red fluorescence (FIG. 1). The light of a red LED (light emitting diode) (FIG. 2) having a wavelength of 635 nm was irradiated on the inflamed site of the nasal mucosa until the red fluorescence could not be visually observed (FIG. 3). More specifically, the red LED light having a wavelength of 635 nm was irradiated for a certain period, followed by discontinuing the PDT irradiation; a bronchoscope (SAFE-3000 from Pentax) was inserted into the nasal cavity by interchanging with the irradiation device; and after observing red light, the PDT irradiation was again performed. As a result, symptoms of a severe runny nose and sneezing were observed in the 3 subjects until several days after the irradiation; however, the symptoms abated over several weeks thereafter. These results suggests that the PpIX accumulating in the inflamed nasal mucosa was excited to generate active oxygen, which resulted in reduced allergenic reactivity due to the degeneration of the epithelium of the nasal mucosa by the active oxygen.

Although PpIX was shown to locally accumulate in an inflamed site of the nasal mucosa, in order to again confirm that simple ALA-PDT could be performed, it was verified whether or not allergic rhinitis could be treated by irradiating red light into the entire nasal cavity using red semiconductor laser light. To a total 12 subjects with pollinosis, 7 adult males and 5 adult females, 20 mg/kg of ALA hydrochloride was orally administered, and 6 hours later, 100 J of red semiconductor laser light having a wavelength of 635 nm was irradiated into the nasal cavity for 6 minutes. As a result, symptoms of a severe runny nose and sneezing due to pollinosis of the 12 subjects disappeared (3 subjects) or abated (5 subjects), and these effects were maintained until at least 1 year after the irradiation. These results show that allergic rhinitis can be treated without specifying an inflamed site of the nasal mucosa.

Example 2

[Treatment of Allergic Rhinitis by Transdermal Administration of ALA]

Then, it was examined whether or not, even when the ALA hydrochloride was administered in an applied liquid form, it could treat allergic rhinitis. A saline solution comprising 5% by weight of ALA hydrochloride sufficiently soaked in cotton was applied to the nasal cavity of 4 adult male subjects with pollinosis, and the soaked cotton was left in place for 1 hour before being removed. 100 J of red semiconductor laser light having a wavelength of 635 nm was intranasally irradiated for 6 minutes immediately after removing the soaked cotton on 3 of the subjects and 1 hour after removing the soaked cotton on the remaining 1 subject. As a result, symptoms of a severe runny nose and sneezing due to pollinosis of the 4 subjects disappeared for the 1 subject irradiated 1 hour thereafter and abated for the 3 subjects irradiated immediately thereafter. These results show that even the administration of ALA hydrochloride in an applied liquid form can treat allergic rhinitis. In addition, the treatment by the liquid form application is shown to be more excellent treatment than that by oral administration in view of cost effectiveness and time effectiveness because the direct application of an ALA hydrochloride solution around an inflamed site of the nasal mucosa can more decrease the amount of ALA hydrochloride administered than oral administration and PpIX accumulates in a short time in the inflamed site of the nasal mucosa.

The invention claimed is:

1. A method of treating allergic rhinitis comprising the following sequential steps (a) to (d);
   (a) administering to a patient in need of treatment for allergic rhinitis a medicine comprising 5-aminolevulinic acid (ALA), an ester derivative thereof, or a salt thereof;
   (b) accumulating PpIX (protoporphyrin IX) induced from 5-aminolevulinic acid (ALA), an ester into cells of an inflamed site of the nasal mucosa of the patient caused by allergic rhinitis;
   (c) irradiating the inflamed site of the nasal mucosa of the patient caused by allergic rhinitis with a light having a wavelength of 400 nm to 700 nm to excite the PpIX; and
   (d) providing a therapeutic effect against allergic rhinitis via singlet oxygen generated by the excited PpIX.

2. The method of treating allergic rhinitis according to claim 1, comprising irradiating an inflamed site of the nasal mucosa of the patient caused by allergic rhinitis with a light having a wavelength of 625 nm to 640 nm.

3. The method of treating allergic rhinitis according to claim 1, wherein the medicine is orally administered.

4. The method of treating allergic rhinitis according to claim 2, wherein the medicine is orally administered.

5. The method of treating allergic rhinitis according to claim 1, wherein the medicine is administered to an inflamed site of a nasal cavity of the patient, wherein the inflamed site is caused by allergic rhinitis.

6. The method of treating allergic rhinitis according to claim 2, wherein the medicine is administered to an inflamed site of a nasal cavity of the patient, wherein the inflamed site is caused by allergic rhinitis.

7. The method of treating allergic rhinitis according to claim 5, wherein the medicine is administered in the form of a solution, a water-soluble ointment, or a jelly.

8. The method of treating allergic rhinitis according to claim 6, wherein the medicine is administered in the form of a solution, a water-soluble ointment, or a jelly.

* * * * *

UNITED STATES PATENT AND TRADEMARK OFFICE
CERTIFICATE OF CORRECTION

PATENT NO. : 9,550,073 B2  
APPLICATION NO. : 14/125744  
DATED : January 24, 2017  
INVENTOR(S) : Tohru Tanaka et al.

Page 1 of 1

It is certified that error appears in the above-identified patent and that said Letters Patent is hereby corrected as shown below:

In the Claims

Column 10, Claim 1, Line 30, "an ester into cells of an" should be --an ester derivative thereof, or a salt thereof specifically into cells of an--.

Signed and Sealed this  
Twenty-seventh Day of June, 2017

Joseph Matal  
*Performing the Functions and Duties of the*  
*Under Secretary of Commerce for Intellectual Property and*  
*Director of the United States Patent and Trademark Office*